United States Patent [19]

Gandy et al.

[11] Patent Number: 4,874,694
[45] Date of Patent: Oct. 17, 1989

[54] USE OF PHOSPHOPROTEIN PATTERNS FOR DIAGNOSIS OF NEUROLOGICAL AND PSYCHIATRIC DISORDERS

[75] Inventors: Samuel E. Gandy; Paul Greengard, both of New York, N.Y.

[73] Assignee: The Rockefeller University, New York, N.Y.

[21] Appl. No.: 35,347

[22] Filed: Apr. 7, 1987

[51] Int. Cl.$^4$ .................. C12Q 1/48; C07G 17/00; C07G 15/00; C07K 3/12
[52] U.S. Cl. .................................... 435/15; 435/267; 435/268; 435/272; 436/63; 436/64; 436/87; 436/177; 530/352; 530/402; 530/412; 530/812; 530/817; 530/828; 530/839; 204/180.1; 204/182.8
[58] Field of Search ................. 435/15, 267, 268, 272; 530/352, 402, 412, 812, 817, 828, 839; 436/63, 64, 87, 177; 204/180.1, 182.8

[56] References Cited

U.S. PATENT DOCUMENTS 4,594,319 6/1986 Sharma .............................. 436/536
4,599,305 7/1986 Witte et al. ......................... 436/536
4,666,829 5/1987 Glenner et al. ..................... 436/501

OTHER PUBLICATIONS

Nestler et al., Science, vol. 225, (1984), pp. 1357-1364.

Primary Examiner—Robert J. Warden
Assistant Examiner—Jack Spiegel
Attorney, Agent, or Firm—Klauber & Jackson

[57] ABSTRACT

A diagnostic method for neurological and psychiatric disorders utilizes the cerebrospinal fluid incubated in the presence of 32-P labelled ATP and an appropriate protein kinase. After termination of the reaction, a sample is applied to gels for electrophoresis. Subsequent autoradiography results in a disease-specific protein pattern that can be used for diagnosis of disorders such as Alzheimer disease, Huntington disease, Parkinson disease, dystonia ataxia, schizophrenia, epilepsy brain tumors, brain irradiation, head trauma, and acute and chronic encephalitic and vascular disease.

12 Claims, 1 Drawing Sheet

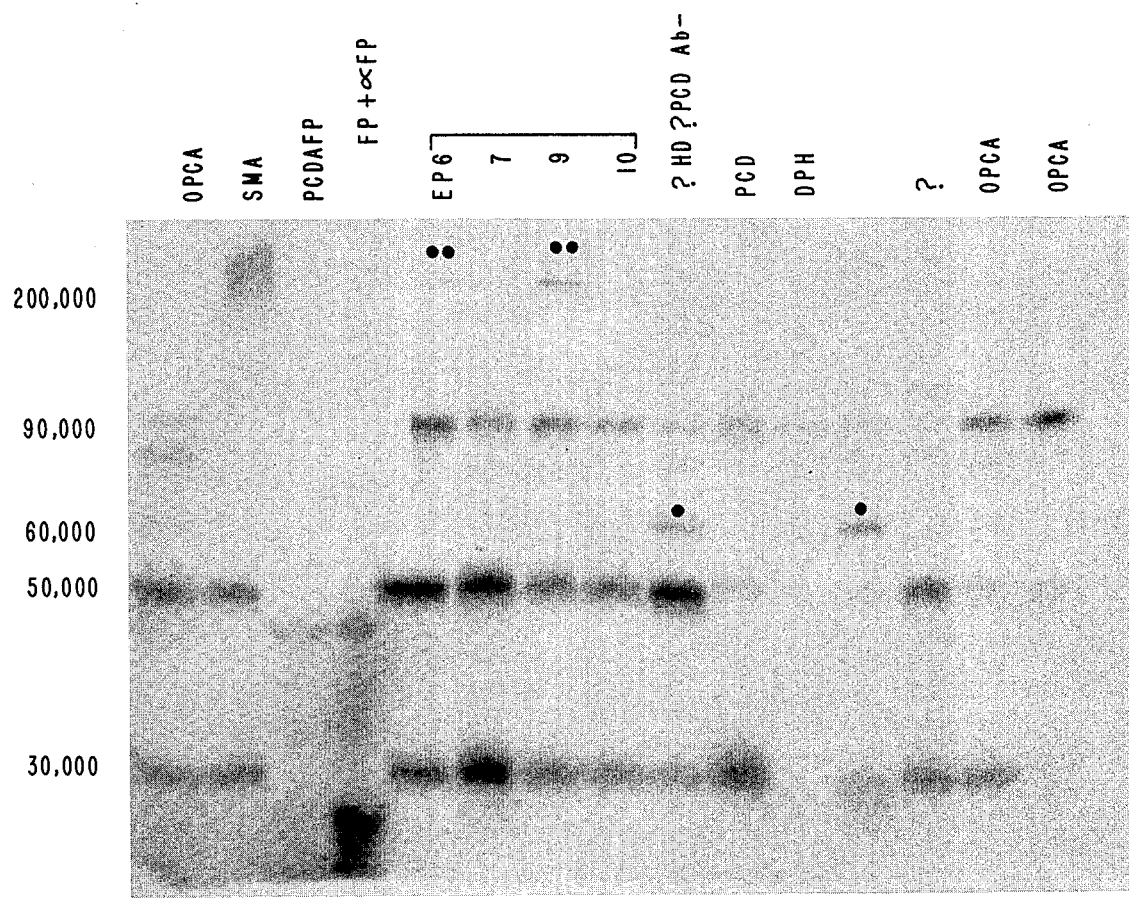
- 60,000 MW BANDS SEEN IN PARANEOPLASTIC ATAXIA
- • 200,000 MW BANDS SEEN IN EPILEPTICS

USE OF PHOSPHOPROTEIN PATTERNS FOR DIAGNOSIS OF NEUROLOGICAL AND PSYCHIATRIC DISORDERS

BACKGROUND OF THE INVENTION

The present invention relates to medical diagnostic techniques, and particularly to methods for identifying certain neurological and psychiatric disorders.

The presence of a great variety of neuron-specific phosphoproteins in nervous tissue supports the view that protein phosphorylation plays many roles in neuronal function. Protein phosphorylation is an important mechanism in neuronal signal transduction. Triggering mechanisms for activation of protein phosphorylation include many established second messengers (cAMP, cGMP, calcium) which are generated by interaction of neurotransmitters with their receptors. The second messengers, in turn, activate protein kinases (protein-phosphorylating enzymes) which transfer phosphate from adenosine triphosphate (ATP) to substrate proteins. These substrate proteins go on to mediate many of the physiological effects attributed to the transmitter-receptor interaction.

The protein composition of cerebrospinal fluid is largely derived from serum proteins which leak into the subarachnoid space through imperfections in the blood brain barrier, such as the area postrema, and perhaps across the choroid plexus, the richly vascular structure through which cerebrospinal fluid is generated as an ultrafiltrate. Some proteins, such as immunoglobulins, may be generated in the subarachnoid space during inflammation. Since the cerebrospinal fluid bathes the surfaces of cerebral and cerebeller cortices, the caudate, brainstem and spinal cord, some contribution of these structures to total cerebrospinal fluid protein might be expected. Indeed, peptide neurotransmitters have been identified in cerebrospinal fluid and are presumably neuron-derived though a serum source has not been excluded. Otherwise, however, cerebrospinal protein chemistry has been notoriously unyielding of neuron-specific information.

Although abnormal proteins have been identified in the cerebrospinal fluid of patients with Creutzfeldt-Jakob disease, See Harrington etal., *New. Eng. J. Med.,* 315, pp 279-283 (1986), no correlative method presently exists which will identify a neurological or psychiatric disorder based upon the proteins present in a patient's cerebrospinal fluid.

SUMMARY OF THE INVENTION

Based on the relative neuronal specificity of the protein kinases and their substrate protein in the cerebrospinal fluid of patients having various neurological and pyschiatric pathologies, it is possible to analyze the cerebrospinal fluid of a patient and determine which particular pathology is present. More particularly, the present invention relates to a method for analyzing the cerebrospinal fluid of a mammal to determine the presence or development of a neurological or psychiatric pathology such as Alzheimer disease, Huntington disease, Parkinson disease, dystonia, ataxia, schizophrenia, epilepsy, brain tumor, brain irradiation, multiple sclerosis, head trauma, acute and chronic encephalitic and vascular disease, which comprises:

(a) incubating a sample of cerebrospinal fluid obtained from said mammal in the presence of 32-P labelled adenosine triphosphate (ATP) and a protein kinase capable of transferring phosphate from the adenosine triphosphate (ATP);

(b) terminating the reaction in (a) after a pre-determined time;

(c) applying a sample of the terminated reaction of (b) to a gel for electrophoresis;

(d) electrophoresing the sampled gel of (c);

(e) performing autoradiography on the electrophoresed gel of (d); and (f) comparing the pattern of the autoradiography of (e) with a set of sample patterns of known neurological and psychiatric pathologies to ascertain the particular pathology of the cerebrospinal fluid being analyzed.

Further this invention relates to the novel disease-specific protein patterns for use in the diagnosis of the aforementioned neurological and pathological disorders in mammals which are produced by:

(a) incubating a sample of cerebrospinal fluid obtained from said mammal in the presence of 32-P labelled adenosine triphosphate (ATP) and a protein kinase capable of transferring phosphate from the adenosine triphosphate (ATP);

(b) terminating the reaction in (a) after a pre-determined time;

(c) applying a sample of the terminated reaction of (b) to a gel for electrophoresis;

(d) electrophoresing the sampled gel of (c); and (e) performing autoradiography on the electrophoresed gel of (d).

This invention additionally concerns a method for preparing patterns for use in the diagnosis of neurological or psychiatric pathologies which method comprises:

(a) incubating a sample of cerebrospinal fluid obtained from a mammal known to be suffering from a neurological or psychiatric disorder in the presence of 32-P labelled adenosine triphosphate (ATP) and a protein kinase capable of transferring phosphate from the adenosine triphosphate (ATP);

(b) terminating the reaction in (a) after a pre-determined time;

(c) applying a sample of the terminated reaction of (b) to a gel for electrophoresis;

(d) electrophoresing the sampled gel of (c);

(e) performing autoradiography on the electrophoresed gel of (d); thereby obtaining a pattern specific for said neurological or psychiatric disorder.

BRIEF DESCRIPTION OF THE DRAWING

The FIGURE is an autoradiogram depicting the results of electrophoresis of samples of cerebrospinal fluid to substantiate the relationships proposed in accordance with the invention.

DETAILED DESCRIPTION OF THE INVENTION

The method of the present invention provides a convenient diagnostic tool for the clinical neurologist to use in the diagnosis of neurological and psychiatric disorders. Many such disorders, especially the degenerative diseases, have heretofor been diagnosed only by brain biopsy or postmortem examinations. Obviously, a simpler, less-invasive technique would be a welcome addition to the diagnostic arts. This invention provides such a diagnostic tool which utilizes only a small sample of the patient mammal's cerebrospinal fluid.

The method of the present invention is based on disease-specific patterns produced by incubating a sample of cerebrospinal fluid in the presence of 32-P labelled adenosine triphosphate (ATP) and a protein kinase capable of transferring phosphate from the adenosine triphosphate. The reaction is then terminated after a predetermined time; and the sample is applied to gel for electrophoresis. After electrophoreses, autoradiography is performed to reveal the radiophosphoylated substrates as a pattern.

It has surprisingly been found that the patterns produced using a particular protein kinase vary with the particular disease state, but do not vary for a group of patients having the same pathology. Thus, the patterns are reproducible for a given disease state and "standard" patterns can be produced for use in diagnosing patients whose particular pathology is unknown or otherwise unconfirmed. These "standard" patterns are produced by obtaining cerebrospinal fluid from a wide range of patients suffering from (or who suffered from) neurological and psychiatric disorders. These neurological and psychiatric disorders are those such as Alzheimer disease, Huntington disease, Parkinson disease, Creutzfeldt-Jakob disease, AIDS dementia, multiinfarct dementia, dystonia, ataxia, epilepsy, schizophenia, Behcet disease, encephalitis, neurosyphylis, cerebral toxoplasmosis, head trauma, brain tumors, brain irradiation, Guillain-Barre syndrome, tremor, and acute and chronic encephalitic and vascular disease.

The protein kinase utilized in the present invention for protein phosphorylation of the protein present in the cerebrospinal fluid sample must be capable of transferring phosphate from the 32-P labelled adenosine triphosphate. Among those protein kinases which can be used are cAMP-dependent protein kinase, protein kinase C (calcium/phospholipid-dependent protein kinase), and calcium-calmodulin-dependent protein kinase. These protein kinases and their role in the phosphorylation of neuronal proteins are described more particularly in Nestler et al., Science, 225, pp 1357-1364 (1984). A particularly preferred protein kinase for use in the present invention is protein kinase C.

The incubation of the cerebrospinal fluid sample of the patient for whom a diagnosis is sought is the first step of the method of the present invention. This incubation of the cerebrospinal fluid sample with 32-P labelled adenosine triphosphate (ATP) and a suitable protein kinase is done according to methods well-known in the art. Specific techniques are detailed in Chapter 4 of "Protein Phosphorylation in the Nervous System", Nestler and Greengard, Jenn Wiley & Sons (1984) and Nestler et al., Science, 225, pp 1357-1364 (1984). Typically, the cerebrospinal fluid sample is mixed with the 32-P labelled adenosine triphosphate in the presence of a catalytic amount of the particular protein kinase and incubated for a predetermined length of time. Typically, this predetermined length of time is about 30 seconds to about five minutes, but it can be further varied depending upon the particular protein kinase being utilized.

The incubation reaction is terminated upon completion of the predetermined length of time. Typically, this is accomplished by the addition of 10% SDS (Sodium dodecyl sulfate), 200 mM EDTA and 10 mM cold ATP to the incubated sample mixture.

Upon completion of the termination of the incubation reaction, the cerebrospinal fluid sample mixture is applied to a suitable support for electrophoresis.

Typically, a polyacrylamide gel is utilized for the electrophoresis, but other support materials, such as filter paper, starch gels or blocks, cellulose or polyurethane foam, may also be used. When other supports are utilized, the patterns will be slightly different, but they will still be consistent for a given pathology.

Typically, the electrophoresis is run on a 10% acrylamide gel at 60 milliamps constant current for a period of 3 to 4 hours. Any standard equipment, such as a Biorad Slab Electrophoresis Unit, can be utilized.

The resultant electrophoresed gels are dried, and then visualized by autoradiography according to methods well-known in the art.

The cerebrospinal fluid of normal humans, after incubation with protein kinase C, shows the substrates for the enzyme as having apparant molecular weight of 90,000, 50,000 and 30,000. A systematic survey of the cerebrospinal fluid of human patients having various neurological and psychiatric disorders, treated with protein kinase C, shows patterns of a different nature, i.e., the visualized bands in the electrophoresed gels are of various other molecular weights.

It is these variations in the band patterns that provide the key to the identity of the particular disease state involved. for instance, the cerebrospinal fluid of patients with paraneoplastic cerebellar degeneration (ataxia), after incubation with protein kinase C in the treatment according to the method of the present invention, exhibits a pattern having a unique band at a molecular weight of 60,000. Similarly, the cerebrospinal fluid of human patients with basal ganglia diseases, after treatment with protein kinase C in the method of the present invention, exhibits a pattern having a family of bands at approximately 200,000 molecular weight. The above-described steps thus result in a visual pattern which can then be compared with the known standards in order to ascertain the particular disease state present in the patient which is the subject of this diagnostic assay.

The following examples describe in detail the methods and techniques illustrative of the present invention. It will be apparent to those skilled in the art that many modifications, both of materials and methods, may be practiced without departing from the purpose and intent of this disclosure.

EXAMPLE I 30 microliter aliquots of cerebrospinal fluid of various origins in 10 microliters of Tris buffer are incubated with 10 microliters portions of [gamma-32P]-adenosine triphosphate (ATP), 10 microliters protein kinase C for a period of one minute. Phosphorylation is then terminated using 30 microliters of a solution of 10% sodium dodecyl sulfate, 200 mM EDTA and 10 mM cold adenosine triphosphate. The entire mixture is then applied to 10% acrylamide gels and subjected to electrophoresis. The electrophoresis is conducted at 60 milliamps constant current for a period of 3.5 hours using a Biorad Slab electrophoresis unit. The electrophoresed gels are dried, and then visualized by autoradiography. The autoradiography is conducted by exposure with a lightening plus screen for 4 hours at −70° C. to produce band patterns characteristic of the disease state involved. The results are depicted in the autoradiogram set forth in the FIGURE to which reference is now made.

The cerebrospinal fluid from normal human patients show a band pattern at the 80,000 molecular weight range.

The cerebrospinal fluid from human patients having paraneoplastic cerebeller degeneration (ataxia) shows a band pattern at about the 60,000 molecular weight.

The cerebrospinal fluid from human patients having basal ganglia diseases (Parkinson's disease, Huntington's disease and dystonia) shows a family of bands pattern at about the 200,000 molecular weight.

The cerebrospinal fluid from human patients having head trauma, and those treated with radiation therapy have a band pattern in the 100,000–200,000 range.

What is claimed is:

1. A method for analyzing the cerebrospinal fluid of a mammal to determine the presence or development of a neurological or psychiatric pathology selected from the group consisting of Alzheimer disease, Huntington disease, Parkinson disease, dystonia, ataxia, schizhrenia, epilepsy, brain tumor, brain irradiation, head trauma, acute and chronic encephalitic and vascular disease, which comprises:
   (a) incubating a sample of said mammalian cerebrospinal fluid in the presence of 32-P labelled adenosine triphosphate (ATP) and a protein kinase capable of transferring phosphate from the adenosine triphosphate (ATP);
   (b) terminating the reaction in (a) after a pre-determined time;
   (c) applying a sample of the terminated reaction of (b) to a gel for electrophoresis to form a sampled gel;
   (d) electrophoresing the sampled gel of (c);
   (e) performing autoradiography on the electrophoresed gel of (d);
   (f) comparing the pattern of the autoradiography of (e) with a set of sample patterns of known neurological and psychiatric pathologies to ascertain the particular pathology of the cerebrospinal fluid being analyzed.

2. The method of claim 1 wherein the protein kinase utilized in step (a) is protein kinase C.

3. The method of claim 1 wherein the pathology is Huntington disease.

4. The method of claim 1 wherein the pathology is Parkinson disease.

5. The method of claim 1 wherein the pathology is epilepsy.

6. The method of claim 1 wherein the pathology is ataxia.

7. A disease specific protein electrophoretic pattern for use in the diagnosis of neurological and pathological disorders, wherein said pattern is produced by the steps comprising:
   (a) incubating a sample of cerebrospinal fluid, obtained from mammals displaying neurological disorders selected from the group consisting of Huntington Disease, Parkinson disease, epilepsy, brain irradiation, head trauma, ataxia associated with paraneoplastic cerebellar degeneration, and dystonia associated with diseases of the basal ganglia, in the presence of 32-P labelled adenosine triphosphate (ATP) and a protein kinase capable of transferring phosphate from the adenosing triphosphate (ATP);
   (b) terminating the reaction in (a) after a pre-determined time;
   (c) applying a sample of the terminated reaction of (b) to a gel for electrophoresis to form a sampled gel;
   (d) electrophoresing the sampled gel of (c); and
   (e) peforming autoradiography on the elecrophoresed gel of (d); thereby obtaining electrophoretic patterns specific for said neurological disorders.

8. A pattern according to claim 7 wherein the protein kinase utilized in step (a) is protein kinase C.

9. A pattern according to claim 7 for the diagnosis of Huntington disease.

10. A pattern according to claim 7 for the diagnosis of Parkinson disease.

11. A pattern according to claim 7 for the diagnosis of epilepsy.

12. A pattern according to claim 7 for the diagnosis of ataxia associated with paraneoplastic cerebellar degeneration.

* * * * *